US008383595B2

(12) United States Patent
Kawabata et al.

(10) Patent No.: US 8,383,595 B2
(45) Date of Patent: Feb. 26, 2013

(54) PEPTIDE DERIVATIVE AND COMPOSITION FOR PROMOTING TEAR SECRETION COMPRISING THE SAME

(75) Inventors: Atsufumi Kawabata, Kashiba (JP); Hiroyuki Nishikawa, Osaka (JP); Kenzo Kawai, Osaka (JP); Yoshiko Kawai, legal representative, Matsubara (JP)

(73) Assignees: Kinki University, Osaka (JP); Fuso Pharmaceutical Industries, Ltd., Osaka (JP)

( * ) Notice: Subject to any disclaimer, the term of this patent is extended or adjusted under 35 U.S.C. 154(b) by 212 days.

(21) Appl. No.: 12/996,728

(22) PCT Filed: Jun. 15, 2009

(86) PCT No.: PCT/JP2009/060873
§ 371 (c)(1),
(2), (4) Date: Dec. 7, 2010

(87) PCT Pub. No.: WO2009/154169
PCT Pub. Date: Dec. 23, 2009

(65) Prior Publication Data
US 2011/0224154 A1    Sep. 15, 2011

(30) Foreign Application Priority Data

Jun. 19, 2008  (JP) ................. 2008-160664

(51) Int. Cl.
*A61K 38/05* (2006.01)
(52) U.S. Cl. ............ 514/21.91; 530/300; 530/323; 530/331; 530/332; 530/333
(58) Field of Classification Search .............. None
See application file for complete search history.

(56) References Cited

U.S. PATENT DOCUMENTS

2003/0203849 A1  10/2003  Araki et al.
2006/0019904 A1   1/2006  Araki et al.

FOREIGN PATENT DOCUMENTS

JP   2001-181208   7/2001
JP   2005-272445  10/2005

OTHER PUBLICATIONS

Facts about the cornea and corneal disease. NEI NIH Health Information 2012.*
Chuang et al. Chang Gung Med J 2006.*
Haeringen, British J Ophth 1997.*
Conjuntivis Prevention, US CDC 2010.*
Takuji et al. *Progress in Medicine*, vol. 26. No. 4, pp. 853-856, 2006.
Takamura. *Refractory Diseases and Home-Care*, vol. 9, No. 12, pp. 61-64, 2004.
Eguchi. *Journal of Clinical and Experimental Medicine*, vol. 199, No. 5, pp. 387-392, 2001.
Nishikawa et al. "Protease-activated receptor-2 (PAR-2)-related peptides induce tear secretion in rats: involvement of PAR-2 and non-PAR-2 mechanisms". *The Journal of Pharmacology and Experiment Therapeutics*, vol. 312, No. 1, pp. 324-331 (2005).
Kawabata et al. "2-Furoyl-LIGRL-$NH_2$, a potent agonist for proteinase-activated receptor-2, as a gastric mucosal cytoprotective agent in mice." *British Journal of Pharmacology*, vol. 144, No. 2, pp. 212-219 (2005).
Kanke et al. "Binding of highly potent protease-activated receptor-2 (PAR2) activating peptide, $^3$[H]2-furoyl-LIGRL- $NH_2$, to human PAR2". *British Journal of Pharmacology*, vol. 145, No. 2, pp. 255-263 (2005).

* cited by examiner

*Primary Examiner* — Anish Gupta
*Assistant Examiner* — Li Lee
(74) *Attorney, Agent, or Firm* — Hamre, Schumann, Mueller & Larson, P.C.

(57) ABSTRACT

A composition for promoting lacrimal secretion which can be used safely and effectively in the lacrimal secretion promoting therapy, not in the conventional supplemental therapy of lacrimal fluid components is provided. The composition for promoting lacrimal secretion comprising a peptide derivative represented by the formula (I):

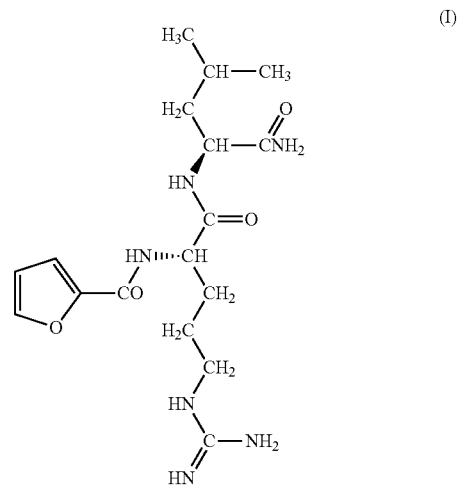

and a contact lens which retains and/or contains the composition are provided.

14 Claims, 5 Drawing Sheets

*P<0.05 vs. physiological saline solution

** $P<0.01$ vs. physiological saline solution

** P<0.01 vs. physiological saline solution

* P<0.05 and **P<0.01 vs. physiological saline solution

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<221> NAME/KEY: AMIDATION
<222> LOCATION: 6
<223> OTHER INFORMATION: Designed control peptide. The C-terminal amino
      acid residue is amidated.

<400> SEQUENCE: 1

Ser Leu Ile Gly Arg Leu
1               5

<210> SEQ ID NO 2
<211> LENGTH: 4
<212> TYPE: PRT
<213> ORGANISM: Artificial Sequence
<220> FEATURE:
<221> NAME/KEY: AMIDATION
<222> LOCATION: 4
<223> OTHER INFORMATION: Designed control peptide. The C-terminal amino
      acid residue is amidated.

<400> SEQUENCE: 2

Ile Gly Arg Leu
1

PEPTIDE DERIVATIVE AND COMPOSITION FOR PROMOTING TEAR SECRETION COMPRISING THE SAME

TECHNICAL FIELD

The present invention relates to a peptide derivative and a composition for promoting lacrimal secretion containing the same for treating and/or preventing an ocular disease accompanied by lowered lacrimal secretion, that are, dry eye, ectocorneal desquamation, corneitis, corneal ulcer, conjunctivitis and the like. Furthermore, the present invention relates to a drug delivery system (DDS) preparation, a percutaneously absorbing preparation, a topical ophthalmic agent (such as eye drops, ophthalmic ointments and the like) and a composition for a contact lens which contain the composition for promoting lacrimal secretion.

BACKGROUND ART

In recent years, dry eye patients have been increased with spread of a contact lens and increase in a VDT-operation. Dry eye is a disease exhibiting symptoms such as xerophthalmia, corneal afflux, foreign body feeling, itching feeling and the like, which results in corneal disorders, in principal, due to lowered lacrimal secretion. In addition, it is said that when dry eye becomes severe, it also causes paropsia and asthenopia.

It is believed as a cause of lowered lacrimal secretion, there are Riley-day syndrome, Shy-Drager syndrome, Sjögren's syndrome, sarcoidosis, amyloidosis, sequela of radiotherapy, lagophthalmos, vitamin A deficiency, Stevens-Johnson syndrome, occular pemphigoid, blepharitis marginal, meibomitis, sequela of intraoccular surgery, contact lens disorder; diabetic ectocorneal disease, VDT-operation, driving over a long period of time and the like (see, PROGRESS IN MEDICINE, 26(4):853-856, 2006, REFRACTORY DISEASES AND HOME-CARE, 9(12):61-64, 2004 and JOURNAL OF CLINICAL AND EXPERIMENTAL MEDICINE, 199(5): 387-392, 2001, for Sjögren's syndrome and a method for treatment thereof).

The lacrimal fluid exists in a border portion where an eyeball contacts with air, and constitutes a thin fluid layer having a thickness of approximately 7 μm which covers an outermost layer of the eyeball. The lacrimal fluid has a three-layered structure, which consists of, from an outer side, an oily layer, an aqueous layer and a mucinous layer, and each layer plays an important role in preventing the eyeball from dryness. The aqueous layer, which occupies most of the lacrimal fluid thickness, is prevented from the decrement by existing between the oily layer and the mucinous layer to maintain the wettability of the eyeball. The oily layer is in principle secreted from a gland existing around an eyelid, which is called meibom gland, and prevents moisture from evaporation by covering throughout the aqueous layer. Accordingly, when the production of the oily layer is reduced due to meibomitis, the aqueous layer becomes apt to evaporate and, thereby, symptom of dry eye is exhibited. The mucinous layer covers a hydrophobic ectocorneal surface to change the surface to hydrophilic and, thereby, has the function of retaining the aqueous layer on an ectocorneal, surface.

The lacrimal fluid has various functions in addition to prevention of dry eye. Other functions of the lacrimal fluid include, for example, protection of cornea and conjunctiva, bacteriostatic action, prevention of infection with bacteria, fungus, virus and the like, feeding of oxygen and a variety of nutritions to cornea and removal of a carbon dioxide gas and metabolites therefrom, dilution and removal of harmful stimuli in the case where cornea and conjunctiva injured, transportation of liquid components such as epidermal growth factors which participate in wound healing and the like and hematocyte components such as fibronectin and the like to the injured portion, retainment of cornea and a conjunctival epithelial cell, regulation of wound healing and the like.

At present, various artificial lacrimal fluid-type eye drops have been sold for the purpose of treatment of lowered lacrimal secretion. However, many of them are a preparation comprising inorganic salts and/or metal chelating agents for the purpose of supplementing the lacrimal fluid and, therefore, although they are temporarily effective to solve the dry feeling of eye followed by lowered lacrimal secretion, the effect is not sustained because they do not affect lacrimal secretion itself. In addition, it is difficult to persistently remove unpleasantnesses such as foreign body feeling and itching upon wearing the contact lens, burning feeling of eye and the like due to dry eye. Furthermore, when those having a lowered amount of oily secretion from meibom gland increase a frequency of the treatment with eye drops, dry feeling of eye becomes stronger due to washing out of the oily and mucinous layers. This attributes to the problem due to a lacrimal fluid components supplementing therapy, but not a lacrimal secretion promoting therapy, which increases lacrimal secretion itself.

As stated above, ophthalmologists and dry eye patients have desired development of a composition for promoting lacrimal secretion which can be used safely and effectively in the lacrimal secretion promoting therapy, not in the conventional lacrimal fluid components supplementing therapy.

For example, JP 2001-181208A discloses an invention in which an peptide having an amino acid sequence: Ser-Leu-Ile-Gly-Arg-Leu-NH$_2$ activates PAR-2 which is a subtype of PAR (Protease-activated receptor) and consequently promoting lacrimal secretion.

In addition, JP 2001-181208A discloses a composition comprising a peptide component consisting of sequential three or four kinds of amino acid of isoleucine (Ile), glycine (Gly), arginine (Arg) and leucine (Leu) as an active center of an excellent lacrimal secretion promoting action.

SUMMARY OF THE INVENTION

The present invention was done in light of the above prior art, and an object of the present invention is to provide a composition for promoting lacrimal secretion which exhibits an effect over a long period of time.

That is, an object of the present invention is to provide a composition having a lacrimal secretion promoting action over a long period of time, which can solve a problem of side effects caused by conventional artificial lacrimal fluid-type eye drops or the like aiming at supplement of lacrimal fluid components.

Particularly, an object of the present invention is to provide a composition which promotes lacrimal secretion over a long period of time by affecting to parasympathetic nerves.

The present inventors have investigated for the purpose of developing a preferable drug as a composition for promoting lacrimal secretion and, as the result, found that lacrimal secretion is caused over a long period of time by a peptide derivative represented by a general formula (I):

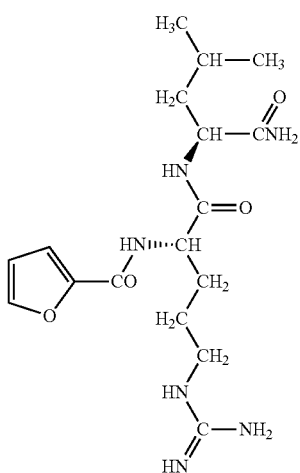

which resulted in completion of the present invention.

That is, the present invention provides

[1] A peptide derivative represented by a formula (I):

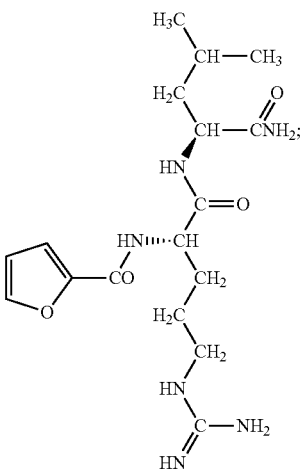

[2] A composition for promoting lacrimal secretion which comprises the peptide derivative of above [1], and is formulated such that it is pharmacologically or pharmaceutically acceptable;
[3] The composition for promoting lacrimal secretion according to above [2], which further comprises a substance that inhibits inactivation or degradation of said peptide derivative;
[4] The composition for promoting lacrimal secretion according to above [3], wherein said substance that inhibits inactivation or degradation is a peptidase inhibitor;
[5] The composition for promoting lacrimal secretion according to above [4], wherein said peptidase inhibitor is amastatin;
[6] The composition for promoting lacrimal secretion according to any one of above [2]-[5], which is formulated into a DDS preparation;
[7] The composition for promoting lacrimal secretion according to any one of above [2]-[6], which is formulated into a percutaneously absorbing preparation;
[8] The composition for promoting lacrimal secretion according to any one of above [2]-[6], which is formulated into a trans-mucosally absorbing preparation;
[9] The composition for promoting lacrimal secretion according to any one of above [2]-[5], which is an ophthalmic composition;
[10] The composition for promoting lacrimal secretion according to above [9], wherein the ophthalmic composition has a form of an eyewash, an eye drop, an ophthalmic ointment, or an ophthalmic gel;
[11] The composition for promoting lacrimal secretion according to above [9], wherein the ophthalmic composition has a form of an eye drop for contact lens, a preserving solution for contact lens or a washing solution for contact lens;
[12] A contact lens which retains and/or contains the composition for promoting lacrimal secretion according to any one of above [2]-[5];
[13] The contact lens according to above [12], which retains and/or contains the composition for promoting lacrimal secretion such that the composition is persistently released;
[14] An agent for treating or preventing an ocular disease, which comprises the composition for promoting lacrimal secretion according to any one of above [2]-[5];
[15] The agent for treating or preventing an ocular disease according to above [14], wherein the ocular disease is dry eye, ectocorneal desquamation, corneitis, corneal ulcer or conjunctivitis.

EFFECT OF THE INVENTION

A peptide derivative and a composition for promoting lacrimal secretion of the present invention exhibit an excellent lacrimal secretion promoting action and, thus, is an excellent therapeutic drug for dry eye resulted from a side effect of a drug, diseases, lowered function of lacrimal secretion or the like. In addition, the composition of the present invention can treat or prevent xerophthalmia, corneal afflux, foreign body feeling, itching feeling, paropsia, asthenopia, unpleasantness, burning feeling and the like followed by dry eye.

In addition, the composition for promoting lacrimal secretion of the present invention may be applied to an eye drop for contact lens, a washing solution for contact lens and a preserving solution for contact lens, or may be applied to a contact lens composition.

DETAILED DESCRIPTION OF THE INVENTION

Figure 1:
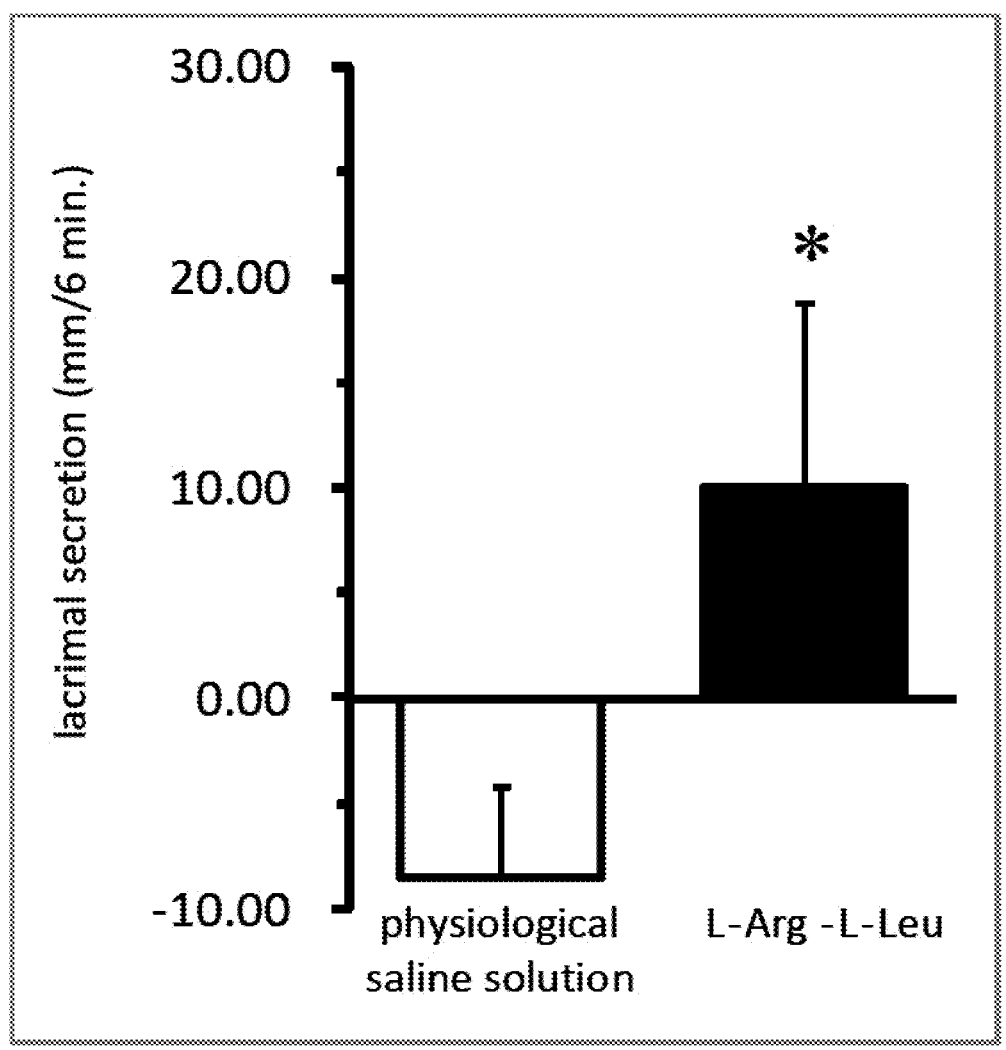
FIG. 1 is a graph showing a promoting action six minutes after administration of (L)Arg-(L)Leu-NH$_2$ on rat lacrimal secretion in vivo.

In the first aspect, the present invention provides a peptide derivative which can exhibits an excellent lacrimal secretion promoting action over a long period of time.

The peptide derivative of the present invention is 2-furoyl-L-arginine (Arg)-L-leucine (Leu), and is represented by the formula (I):

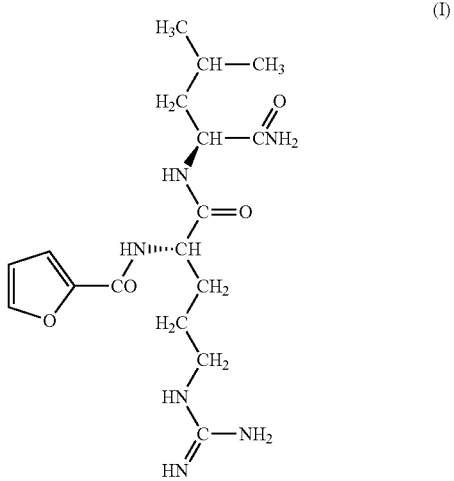

and has following physical properties.

$^1$H-NMR (D$_2$O):0.605 (d, 3H, J=6.2 Hz), 0.656 (d, 3H, J=6.2 Hz), 1.307-1.742 (m, 7H), 2.973 (t, 2H, J=6.9 Hz), 4.106 (dd, 1H, J=10.2, 4.4 Hz), 4.250 (dd, 1H, J=8.4, 6.0 Hz), 6.378 (dd, 1H, J=3.7, 1.8 Hz), 6.947 (dd, 1H, J=3.7, 0.7 Hz), 7.426 (dd, 1H, J=1.8, 0.7 Hz).

Elementary analysis calculated for C$_{17}$H$_{28}$N$_6$O$_4$: C, 53.67; H, 7.42; N, 22.09; O, 16.82.

Mass spectrometry
Calculated: 380.44
Found: 380.22

The peptide derivative of the present invention may be synthesized according to a known method described by Carpino, L. A. et al., J. Org. Chem., 37, 3404-3409, 1972.

Briefly, for L-Arg-L-Leu-NH$_2$, D-Arg-L-Leu-NH$_2$, L-Arg-D-Leu-NH$_2$ and D-Arg-D-Leu-NH$_2$, dimethylformamide is added to a commercially-available Fmoc-PAL-PEG-PS-resin to stand, and the resin is swollen and filled in a column for peptide synthesis. Then, Fmoc-L-Leu-OH, Fmoc-D-Leu-OH, Fmoc-L-Arg(Pbf)-OH and/or Fmoc-D-Arg (Pbf)-OH is strictly weighted, and HATU (O-(7-azabenztriazol-1-yl)-1,1,3,3-tetramethyluronium hexafluorophosphate) is added thereto. Amino acids described above are placed in an order from the C-terminal, and synthesis of the peptide derivative is performed with a peptide synthesizer. A peptide resin synthesized is treated with a mixed solution of trifluoroacetic acid (TFA), water and triisopropylsilane, and then filtrated. The filtrate is recrystallized from cold diethyl ether to obtain a crude peptide. The crude peptide is purified with a high performance liquid chromatography (HPLC), and a resulting fraction is lyophilized to obtain the aimed peptide.

In addition, for cyclo-L-Arg-L-Leu-NH$_2$, L-Leu-PS-resin is weighted and dimethylformamide is added thereto to stand, and the resin is swollen and filtrated. To this resin, Fmoc-L-Arg (Pbf)-OH, N,N-diisopropylethylamine, HATU (O-(7-azabenztriazol-1-yl)-1,1,3,3-tetramethyluronium hexafluorophosphate) is added, and they are agitated and filtrated, and the resin is washed with an appropriate amount of dimethylformamide. In addition, piperidine and dimethylformamide (2:8) are added to them and they are agitated. The resin is filtrated and washed with an appropriate amount of dimethylformamide. A peptide-resin synthesized is treated with a mixed solution of TFA, water and triisopropylsilane (8.8:5.0:0.5:0.2), and then filtrated. The filtrate is cyclized and then recrystallized from cold diethyl ether to obtain a crude peptide. The crude peptide is purified with the HPLC, and a resulting fraction is lyophilized to obtain the aimed peptide.

In addition, for N-(2-furoyl)-L-Arg-L-Leu-NH$_2$, Fmoc-PAL-PEG-PS-resin is weighted and dimethylformamide is added thereto to stand, and the resin is swollen and filled in a column for peptide synthesis. A column for peptide synthesis is prepared according to the above method. Fmoc-L-Leu-OH and Fmoc-L-Arg (Pbf)-OH are weighted, and HATU (O-(7-azabenztriazol-1-yl)-1,1,3,3-tetramethyluronium hexafluorophosphate) is added thereto. Amino acids described above are placed in an order from the C-terminal, and synthesis of the peptide derivative is performed with a peptide synthesizer. A peptide-resin synthesized is removed from the peptide synthesizer, and filtrated while washing it with dichloromethane. To this peptide-resin, 2-furoic acid, N,N-diisopropylethylamine and HATU (O-(7-azabenztriazol-1-yl)-1,1,3,3-tetramethyluronium hexafluorophosphate) are added. The resin is filtrated after agitation, and washed with an appropriate amount of dimethylformamide. To this resin, piperidine and dimethylformamide (2:8) are further added and agitated, and then the resin is filtrated and washed with an appropriate amount of dimethylformamide. A peptide-resin synthesized is treated with a mixed solution of TFA, water, phenol and triisopropylsilane (8.8:5.0:0.5:0.2), and then filtrated. The filtrate is recrystallized from cold diethyl ether to obtain a crude peptide. Then, the crude peptide is purified with the HPLC, and a resulting fraction is lyophilized to obtain the aimed peptide.

The peptide derivative of the present invention also includes a pharmaceutically acceptable salt thereof.

The pharmaceutically acceptable salt includes, for example, salts with bases such as an inorganic base and an organic base, and acid addition salts with acids such as an inorganic acid, an organic acid and a basic or acidic amino acid and the like. The inorganic base includes, for example, alkali metals such as sodium, potassium and the like, alkaline-earth metals such as calcium, magnesium and the like, and aluminum, ammonium and the like. The organic base includes, for example, primary amines such as ethanolamine and the like, secondary amines such as diethylamine, diethanolamine, dicyclohexylamine and N,N'-dibenzylethylenediamine and the like, tertiary amines such as trimethylamine, triethylamine, pyridine, picoline, triethanolamine and the like, and the like. The inorganic acid includes, for example, hydrochloric acid, hydrobromic acid, nitric acid, sulfuric acid, phosphoric acid and the like. The organic acid includes, for example, formic acid, acetic acid, lactic acid, trifluoroacetic acid, fumaric acid, oxalic acid, tartaric acid, maleic acid, benzoic acid, citric acid, succinic acid, malic acid, methanesulfonic acid, ethanesulfonic acid, benzenesulfonic acid, p-toluenesulfonic acid and the like. The basic amino acid includes, for example, arginine, lysine, ornithine and the like. The acidic amino acid includes, for example, aspartic acid, glutamic acid and the like.

In the second aspect, the present invention provides a composition for promoting lacrimal secretion which comprises the peptide derivative aforementioned and is formulated such that it is pharmacologically or pharmaceutically acceptable.

The composition for promoting lacrimal secretion of the present invention is useful as an agent for treatment or prevention of ocular diseases such as dry eye, ectocorneal desquamation, corneitis, corneal ulcer, conjunctivitis and the like, which can be treated or prevented. When the composition is used as the treating or preventing agent, the composition for promoting lacrimal secretion of the present invention can be used as such or can be used after various treatments such as dilution with water and the like. Also, the composition for promoting lacrimal secretion can be used by incorporation in a drug or a quasi-drug, particularly in a composition for eye drops, a transmucosally absorbing preparation, a percutaneously absorbing preparation or the like. An amount of the peptide derivative to be incorporated may be appropriately selected depending on a product, but may be usually 0.001-50% by weight, and particularly 0.01-10% by weight in the case of a systemic administration preparation. When the amount is below 0.001% by weight, there is a possibility that a satisfactory lacrimal secretion promoting action is not observed. On the other hand, when the amount exceeds 50% by weight, there is a possibility that properties of the product itself such as the stability, the flavoring property and the like are deteriorated.

An amount of lacrimal secretion which is an indication for determining an effect of promoting lacrimal secretion can be measured according to a known method such as by Iga et al. (Iga, Y. et al., Jpn. J. Pharmacol., 78, 373-80, 1998) using a rat. In particular, a rat is anesthetized with pentobarbital (50 mg/kg, intra-abdominal administration), and a paper with 2 mm width for testing the human lacrimal secretion function, the Schirmer test paper (Showa Yakuhin Kako Co., Ltd.) is inserted into a lower eyelid of the rat. After a fixed period of time has passed, the test paper is removed, and a length of the wetted portion of the test paper is measured using a caliper square. If a statistically significant increase of lacrimal secretion is observed when a test substance is administered, it can be said that the substance has the lacrimal secretion promoting action.

A durability of the peptide derivative contained in the composition for promoting lacrimal secretion of the present invention can be enhanced by using together with a drug such as amastatin and the like, a peptidase inhibitor, or by incorporating amastatin into the composition, because the peptide derivative is degraded by a peptidase existing in a living body or externally administrated.

As a mode of administrating a composition for promoting lacrimal secretion of the present invention, oral, topical ocular, intravenous, transmucosal, transdermal, intramuscular, subcutaneous, or rectal administration or the like can be properly selected, and the composition of the present invention can be formulated into various preparations depending on the mode of the administration.

Although each preparation is described below, a dosage form used in the present invention is not limited thereto, and the composition of the present invention can be used as various kinds of preparations which are ordinarily used in the field of pharmaceutical preparation.

Systemic Administration Preparation

When the composition of the present invention is used as a drug for treating lowered lacrimal secretion, an oral dosage of the peptide derivative is preferably in a range of 3-300 mg/kg, and more preferably in a range of 10-100 mg/kg. When the systemic administration of the composition is conducted, particularly when it is intravenously administered, the component should be administered such that the effective blood concentration thereof becomes in a range of 2-200 µg/mL, more preferably in a range of 5-100 µg/mL, although it may vary depending on sex, age and body type of the subject.

When the composition is orally administered, the dosage form of the composition can be properly selected from the group consisting of powders, granules, capsules, pills, tablets, elixirs, suspensions, emulsions, syrups and the like. In addition, modification such as sustained-releasing, stabilizing, easy-disintegrating, hard-disintegrating, enterally solubilizing, and easy-absorbing properties and the like may be applied to such the preparation depending on the purpose. The dosage form in the case of the oral administration includes, for example, chew, sublingual, buccal, lozenges, ointments, attaching preparations, solution and the like, and it can be properly selected therefrom. In addition, modification such as sustained-releasing, stabilizing, easy-disintegrating, hard-disintegrating, enterally solubilizing, and easy-absorbing properties and the like may be applied to such the preparation.

Known DDS techniques can be adopted to each dosage form as described above. The term DDS preparation herein refers to a preparation having an optimal form in light of an administration route, bioavailability, a side effect or the like, such as a sustained-releasing preparation, a topically applying preparation (such as a lozenge, a buccal tablet, a sublingual tablet and the like), a controlled-releasing preparation, an enteric soluble preparation, a gastric soluble preparation and the like.

Basically, as constituents of DDS, there are a drug, a drug-releasing module, a film, and a therapeutic program. Particularly, for each constituent, the drug has preferably a short half-life such that the blood concentration of the drug is quickly lowered when the releasing thereof is stopped, the film is preferably not reactive with a biological tissue at the administered portion, and the therapeutic program preferably maintains the excellent drug concentration during a predetermined period. Basically, the drug-releasing module has a drug reservoir, a release-controlling portion, an energy source and a releasing port or a releasing surface. These basic constituents may not be all supplemented at the same time, and some of them may be optionally added or omitted to select the excellent form of DDS.

The material to be used for DDS includes polymers, cyclodextrin derivatives, lecithin and the like. The polymers include an insoluble-polymer (silicone, ethylene-vinyl acetate copolymer, ethylene-vinyl alcohol copolymer, ethyl cellulose, cellulose acetate and the like), a water-soluble polymer and a hydroxyl gel-forming polymer (polyacrylamide, a cross-linked polyhydroxyethyl methacrylate polymer, a cross-linked polyacrylic polymer, polyvinyl alcohol, polyethylene oxide, a water-soluble cellulose derivative, cross-linked poloxamer, chitin, chitosan and the like), a gradually-dissolving polymer (ethyl cellulose, a partial ester of methyl vinyl ether-malic anhydride copolymer and the like), a gastric-soluble polymer (hydroxypropylmethyl cellulose, hydroxypropyl cellulose, carmellose sodium, macrogol, polyvinyl pyrrolidone, dimethylaminoethyl methacrylate-methyl methacrylate copolymer and the like), enteric polymer (hydroxypropylmethyl cellulose phthalate, cellulose acetate phthalate, hydroxypropylmethyl cellulose acetate succinate, carboxymethylethyl cellulose, acrylates polymer and the like), and a bio-degradable polymer (thermocoagulated- or -cross-linked albumin, cross-linked gelatin, collagen, fibrin, polycyanoacrylate, polyglycolic acid, polylactic acid, poly-β-hydroxyacetic acid, polycaprolactone and the like), and may be properly selected depending on the dosage form.

Particularly, silicone, ethylene-vinyl acetate copolymer, ethylene-vinyl alcohol copolymer, and a partial ester of methyl vinyl ether-maleic anhydride copolymer may be used for controlling release of a drug, cellulose acetate may be used as a material of an osmotic pump, ethyl cellulose, hydroxypropylmethyl cellulose, hydroxypropyl cellulose and methyl cellulose may be used as a film raw material of the sustained-release preparation, and the cross-linked polyacryl polymer may be used as an adsorbing agent to oral or ophthalmic mucosa.

In addition, the preparation can be produced by adding additives such as solvents, excipients, coating agents, bases, binding agents, lubricants, disintegrating agents, solution adjuvants, suspending agents, thickening agents, emulsifying agents, stabilizing agents, buffering agents, isotonicity adjusting agents, soothing agents, preservatives, corrigents, flavors, coloring agents and the like thereto depending on the dosage form thereof (known dosage form such as oral preparation, injections, suppository, percutaneously absorbing preparation and the like).

Each of these additives is specifically exemplified below, but is not limited thereto.

Solvents include, for example, purified water, water for injection, physiological saline solution, peanut oil, ethanol, glycerin and the like.

Excipients include, for example, starches, lactose, dextrose, white sugar, crystalline cellulose, calcium sulfate, calcium carbonate, talc, titanium oxide, trehalose, xylitol and the like.

Coating agents include, for example, white sugar, gelatin, cellulose acetate phthalate and polymers as described above and the like.

Bases include, for example, vaseline, vegetable oils, macrogol, an oil-in-water emulsion base, an water-in-oil emulsion base and the like.

Binding agents include, for example, starch and derivatives thereof, cellulose and derivatives thereof, naturally-occurring polymer compounds such as gelatin, sodium alginate, tragacanth, gum arabic and the like, synthetic polymer compounds such as polyvinyl pyrrolidone and the like, dextrin, hydroxypropyl starch and the like.

Lubricants include, for example, stearic acid and salts thereof, talc, waxes, wheat starch, macrogol, hydrogenated vegetable oils, sucrose fatty acid esters, polyethylene glycol and the like.

Disintegrating agents include, for example, starch and derivatives thereof, agar, gelatin powder, sodium hydrogen carbonate, cellulose and derivatives thereof, carmellose calcium, hydroxypropyl starch, carboxymethyl cellulose and salts thereof as well as cross-linked polymers thereof, low-substituted hydroxypropyl cellulose and the like.

Solution adjuvants include, for example, cyclodextrin, ethanol, propylene glycol, polyethyleneglycol and the like.

Suspending agents include, for example, gum arabic, tragacanth, sodium alginate, aluminum monostearate, citric acid, various surfactants and the like.

Thickening agents include, for example, carmellose sodium, polyvinyl pyrrolidone, methyl cellulose, hydroxypropylmethyl cellulose, polyvinyl alcohol, tragacanth, gum arabic, sodium alginate and the like.

Emulsifying agents include, for example, gum arabic, cholesterol, tragacanth, methyl cellulose, various surfactants, lecithin and the like.

Stabilizing agents include, for example, sodium hydrogen sulfite, ascorbic acid, tocopherol, chelating agents, inert gas, reducing substances and the like.

Buffering agents include, for example, sodium hydrogenphosphate, sodium acetate, boric acid and the like.

Isotonicity adjusting agents include, for example, sodium chloride, glucose and the like.

Soothing agents include, for example, procaine hydrochloride, lidocaine, benzyl alcohol and the like.

Preservatives include, for example, benzoic acid and salts thereof, paraoxybenzoic acid esters, chlorobutanol, invert soap, benzyl alcohol, phenol, thimerosal and the like Corrigents include, for example, white sugar, saccharin, licorice extracts, sorbitol, xylitol, glycerin and the like.

Flavors include, for example, bitter tincture, rose oil and the like.

Coloring agents include, for example, water-soluble edible pigments, lake pigments and the like.

As described above, effects such as the sustained effective blood concentration of a drug, enhancement of bioavailability and the like can be expected by formulating a pharmaceutical into a DDS preparation such as a sustained-releasing preparation, an enteric preparation, a drug controlled-releasing preparation and the like. However, there is a possibility that an active peptide and/or a lacrimal secretion promoting peptide is inactivated or degraded in a living body and, as the result, the desired effect is lowered or disappeared. For example, it is known that many of the peptides are degraded by aminopeptidase in a living body (Godin, D. et al., Eur. J. Pharmacol., 253, 225-30, 1994). Accordingly, a substance, which inhibits another substance which inactivates or degrades the active peptide and/or the lacrimal secretion promoting peptide (for example, a substance which inhibits aminopeptidase), may be used together with the composition for promoting lacrimal secretion of the present invention to further sustain the effects of the component.

Amastatin, Arphamenine A, Arphamenine B, bestatin and the like are known as an aminopeptidase inhibitor. These compounds may be incorporated in the preparation, or may be administered apart from the preparation. When the above component is not a peptide, those skilled in the art can properly identify a substance which inactivates or degrades the component, select another substance which inhibits the substance, and can incorporate the substance in the preparation or use together with the preparation.

Ingredients other than those described above, which are used in the conventional composition as an additive, may be used in the preparation. An amount of these ingredients to be added may be a usual amount without deteriorating the effect of the present invention.

The composition for promoting lacrimal secretion of the present invention can be also applied to the skin. A preparation to be applied to the skin is not particularly limited to, but includes lotions, creams, gels, ointments, paste, plaster, attaching preparations, patch, cataplasm, tape, TTS (Transdermal Therapeutic System) preparations and the like. An application site is not particularly limited to, but includes breast, nether parts, regions of back, leg, cheek, eyelid, lower eyelid, arm, neck and the like. A percutaneously absorbing preparation herein refers to all the preparations as described above in a broader sense, but refers to a preparation having a support such as plaster, attaching preparations, patch, cataplasm, tape, TTS preparations and the like in a narrower sense.

Particularly, a sticky polymer which is used for the percutaneously absorbing preparation having a support includes acrylic series, rubber series, silicone series and the like, but is not particularly limited thereto so long as it is biologically acceptable.

As the acrylic series, although (co) polymers containing alkyl (meth)acrylate as a main component may be suitably used, copolymers of alkyl (meth)acrylate and a monomer which is copolymerizable with said alkyl (meth)acrylate may be used. A ratio of alkyl (meth)acrylate in the constituents of (co)polymers containing alkyl (meth)acrylate as a main component is preferably equal to or higher than 20% by weight.

Alkyl (meth)acrylates include methyl acrylate, butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, butyl methacrylate, isobutyl methacrylate, 2-ethylhexyl methacrylate, isooctyl methacrylate, decyl methacrylate, isodecyl methacrylate, lauryl methacrylate, stearyl methacrylate and the like, and they may be used alone or in combination thereof.

The polymerizable monomer as described above is preferably a functional monomer such as a monomer containing an alkoxy group having an ether linkage on a side chain, a monomer having a hydroxy group, a monomer having a carboxyl group, a monomer having an amido group, a monomer having an amino group, a monomer having a sulfoxyl group, a monomer having an alkoxy group, a monomer having a nitrogen-containing heterocycle and the like. Embodiments of such the monomer are described below.

The monomers containing an alkoxy group having an ether linkage on a side chain include, for example, methoxyethyl (meth)acrylate, ethoxydiethyl (meth)acrylate, methoxydiethyleneglycol (meth)acrylate, methoxypropylene glycol (meth)acrylate and the like.

The monomers having a hydroxy group include, for example, hydroxyalkyl (meth)acrylates such as hydroxyethyl (meth)acrylate, hydroxypropyl (meth)acrylate and the like.

The monomers having a carboxyl group include, for example, $\alpha$ or $\beta$-unsaturated carboxylic acids such as (meth)acrylic acid and the like, monoalkyl maleates such as butyl maleate and the like, maleic acid (anhydride), itaconic acid, fumaric acid, crotonic acid and the like.

The monomers having an amido group include, for example, alkyl (meth)acrylamides such as (meth)acrylamide, dimethyl (meth)acrylamide, N-butylacrylamide, diethylacrylamide and the like, N-alkoxy (methyl)acrylamides such as butoxymethylacrylamide, ethoxymethylacrylamide and the like, and the like.

The monomers having an amino group include, for example, dimethylaminoacrylate and the like.

The monomers having a sulfoxyl group include, for example, styrenesulfonic acid, acrylsulfonic acid, sulfopropyl (meth)acrylate, (meth)acryloyloxynaphthalenesulfonic acid, acrylamidemethylpropanesulfcnic acid and the like.

The monomers having an alkoxy group include, for example, methoxyethyl (meth)acrylate, tetrahydrofurfuryl (meth)acrylate, methoxyethyleneglycol (meth)acrylate, methoxypolyethyleneglycol (meth)acrylate and the like.

The monomers having a nitrogen-containing heterocycle include, for example, vinylpyrrolidone, methyl vinylpyrrolidone, vinylpiperazine, vinylimidazole and the like.

In addition to the monomers as described above, monomers such as vinyl chloride, vinyl acetate, vinyl propionate, styrene, $\alpha$-methylstyrene, acrylonitrile, ethylene, propylene, butadiene and the like may be used.

The (co)polymer containing alkyl (meth)acrylate as a main component as described above is usually prepared by conducting solution polymerization, in which the monomer as described above is contained in the presence of a polymerization initiator. In the case where solution polymerization is conducted, a solvent for polymerization such as ethyl acetate and the like may be added to a predetermined amount of various monomers, and the mixture may be reacted, under the nitrogen atmosphere, at 50-90° C. for 5-100 hours in a reaction vessel equipped with a stirrer and a condenser in the presence of a polymerization initiator such as azobis- and peroxide-compounds and the like.

The organic solvents for polymerization include, for example, benzene, ethylbenzene, butylbenzene, toluene, xylene, hexane, heptane, ethyl acetate, hydroxyethyl acetate, methyl benzoate, acetone, methyl cellosolve, ethyleneglycol monoethyl ether, methyl alcohol, propyl alcohol and the like. The azobis polymerization initiators include 2,2-azobis-isobutyronitrile, 1,1'-azobis(cyclohexane-1-carbonitrile), 2,2'-azobis(2,4-dimethylvaleronitrile) and the like, and the peroxide polymerization initiators include, for example, lauroyl peroxide, benzoyl peroxide and the like.

As the rubber series adhesive as described above, for example, natural rubber, isoprene rubber, polyisobutylene, polyvinyl ether, polyurethane, polyisoprene, polybutadiene, styrene-butadiene copolymer, styrene-isoprene copolymer, styrene-isoprene-styrene block copolymer and the like may be used.

As the silicone series adhesive as described above, for example, silicone rubber such as of polyorgano-siloxane and the like may be used.

In addition, as the adhesive, those generally used for preparing a percutaneously absorbing preparation, such as described in JP 9-208605A, JP 10-94595A, JP 10-94596A, JP 10-298068A and the like may be used.

A layer of the adhesive as described above may be formed on a sheet- or tape-shaped support. As the support, those in which an amount of the percutaneously absorbing drug contained in a layer of the adhesive is not lowered due to the loss of the drug through a backside of the support, that is, those comprised of a drug non-permeable material may be suitably utilized.

As the support, films such as of nylon, polyvinyl chloride, plasticized polyvinyl chloride, polyvinylidene chloride, polyethylene, polyethylene terephthalate, polypropylene, cellulose acetate, ethyl cellulose, plasticized vinyl acetate-vinyl chloride copolymer, ethylene-vinyl acetate copolymer, ethylene-ethyl acrylate copolymer and polyurethane, a polyester/polyethylene-vinyl acetate copolymer laminate, a polyethylene-vinyl acetate copolymer/rayon nonwoven fabric laminate, a polyester nonwoven fabric/polyester film laminate, a vinylon nonwoven fabric/polyester film laminate (particularly, see JP 10-310521A) and films such as of an aluminum sheet and the like may be used, and these materials may be used as a single layer or a laminate comprised of two or more thereof. A thickness of the support is preferably equal to or smaller than 2000 µm, and more preferably 2-300 µm.

The composition for promoting lacrimal secretion of the present invention may be contained in finely-divided polymer particles dispersed in a layer of the adhesive. The finely-divided polymer particle is, for example, of cross-linked polyvinyl pyrrolidone, cross-linked cellulose, polystyrene, styrene-divinylbenzene copolymer or the like, and the material of the finely-divided polymer particle is properly selected depending on a kind of a drug and the like. A diameter of the finely-divided polymer particle is preferably equal to or smaller than 200 µm, and more preferably equal to or smaller than 50 µm. The drug contained in the finely-divided polymer particle may be existed in the solubilized or un-solubilized state. The solvent to be used for incorporating a drug in the finely-divided polymer particle may be properly selected depending on a kind of a drug or finely-divided polymer particle, and examples thereof include ethyl acetate, toluene, tetrahydrofuran and the like.

In preparation of the percutaneously absorbing preparation of the present invention, conventional methods for producing an adhesive tape can be applied for forming a layer of the adhesive, such as a solvent coating method, a hot-melt coating method, an electron radiation curing emulsion coating method and the like.

In the solvent coating method as described above, a layer of the adhesive having a predetermined thickness can be formed on a support by dissolving or dispersing an adhesive, a drug and, if necessary, other additive in a suitable solvent, coating the resulting solution or dispersion on the surface of the support, and then drying it to remove the solvent. Alternatively, a layer of the adhesive may be prepared by coating the solution or dispersion as described above on a release paper and adhering the resulting layer of the adhesive on the surface of a support after drying. If necessary, the percutaneously absorbing preparation in which a finely-divided polymer particle containing a drug is dispersed in a layer of the adhesive can be obtained by using a finely-divided polymer particle containing a drug in advance. The solvents to be used include, for example, benzyl alcohol, butyl benzoate, isopropyl myristate, octanol, propylene glycol, polypropylene glycol, ethylene glycol and the like.

Alternatively, the solution or dispersion as described above may be applied to a release paper on which a silicone resin or the like is coated, and the release paper is dried and adhered to a support, without directly applying the solution or dispersion to the surface of the support. Such the release paper may be used for protecting the surface of a layer of the adhesive of the percutaneously absorbing preparation such as of tape and the like until use. For example, a release paper in which the surface of a polyethylene terephthalate film is treated with silicone may be used. A thickness of the release paper is preferably equal to or smaller than 1000 μm, and more preferably 10-300 μm.

A thickness of a layer of the adhesive may vary depending on an object of use and an application site and, when a thickness becomes small, an adhering force thereof becomes weak, and the content of a drug per unit area of the percutaneously absorbing preparation becomes insufficient. On the other hand, when a thickness becomes large, there is a possibility that a drug-releasing rate is lowered since a drug contained in a layer of the adhesive near a support does not sufficiently diffuse. Specifically, a layer of the adhesive is prepared such that it has a thickness of preferably 3-1000 μm, and more preferably 10-500 μm. In addition, a crosslinking treatment may be applied to a layer of the adhesive.

If necessary, additives such as plasticizers, absorption-promoting agents, skin irritation reducing agents, antioxidants and the like may be added to a layer of the adhesive. An amount of the additive to be used varies depending on a kind of the additive and is preferably 1-50% by weight, and more preferably 1-10% by weight based on a total weight of a layer of the adhesive. When the amount of the additive to be used is smaller than 1% by weight, an adhering force-lowering action becomes small. On the other hand, when the amount exceeds 50% by weight, there is a possibility that an adhering force to a skin becomes too weak, adhesive transfer is caused due to lowering of cohesion or the like.

A plasticizer can regulate an adhering force of a layer of the adhesive to the skin and reduce irritation upon peeling off from the skin. The plasticizer includes, for example, diisopropyl adipate, phthalic acid ester, diethyl sebacate, higher fatty acid esters, a softening agent described in JP 10-179711A and the like, and they may be used by mixing two or more thereof.

An absorption-promoting agent includes a compound which enhances the solubility or the dispersibility of a drug in a layer of the adhesive, a compound which changes a water-retaining ability of keratin, a keratin-softening ability, a keratin-permeability, or the like, a compound which acts as a carrier and the like.

The compound which enhances the solubility or the dispersibility includes glycols such as ethylene glycol, diethylene glycol, propylene glycol, triethylene glycol, polyethyleneglycol, polypropylene glycol and the like, oils and fats such as olive oil, caster oil, squalene, lanolin and the like, and the like. The compound which changes the water-retaining ability of keratin, the keratin-softening ability, the keratin-permeability includes 1-dodecylazocycloheptane-2-one, oleic acid, isopropyl myristate, middle-chain fatty acid monoglyceride, monoterpenes, l-menthol, d-limonene urea, allantoin, salicylic acid, methyloctyl sulfoxide, dimethyllaurylamine, dodecylpyrrolidone, iso-sorbitol, dimethylacetamide, dimethyl sulfoxide, dimethylformamide and the like. The compound which acts as a carrier includes, for example, ethanol, iso-propanol, N-methyl-2-pyrrolidone, propylene glycol and the like. In addition, benzyl nicotinate which is a hair pore opening agent, dibutylhydroxytoluene which is an antioxidant, and the like may be used. An additive or synergistic absorption-promoting effect can be expected by using two or more of absorption-promoting agents as described above together.

Besides, the additive includes hydrocarbons, various surfactants, aliphatic alcohols such as myristyl alcohol, pentadecyl alcohol, cetyl alcohol, heptadecyl alcohol, stearyl alcohol and the like, straight-chain fatty acids such as pentadecanoic acid, palmitic acid, heptadecanoic acid, stearic acid, oleic acid and the like, and aliphatic esters such as methyl oleate, ethyl oleate, propyl oleate, methyl stearate, ethyl stearate, propyl stearate, butyl stearate, lauryl stearate, myristyl stearate, nonadecanoic acid methyl ester and the like, and the like.

A method for crosslinking includes a physical crosslinking treatment with radiation such as ultraviolet ray, electron beam, X-ray, β-ray, γ-ray and the like, and a chemical crosslinking treatment which uses crosslinking agents such as polyisocyanate compounds, organic peroxides, organometallic salts, metal alcoholates, metal-chelating compounds, isocyanate compounds, epoxy compounds and the like. An amount of the crosslinking agent to be added in a layer of the adhesive is 0.001-10%, and preferably 0.05-1%.

An amount of a drug to be contained in the percutaneously absorbing preparation is properly set depending on a kind of a drug and an application site and is usually in a range of 1-60% by weight, preferably 2-40% by weight. When the content of a drug in the percutaneously absorbing preparation is below 1% by weight, release of a drug at an effective amount for treatment or prevention can not be expected. On the other hand, when the content of a drug exceeds 60% by weight, it is economically disadvantageous because enhancement of the effect can not be expected for increment of a drug. In addition, in the present invention, a whole drug contained in the percutaneously absorbing preparation is not necessarily dissolved in a layer of the adhesive, and a drug can be contained at an amount equal to or exceeding its solubility in a layer of the adhesive and dispersed in the undissolved state.

As the known techniques of percutaneously absorbing preparations, there are those described in JP 9-77658A, JP 9-12448A, JP 9-176000A, JP 9-301853A, JP 9-169635A, JP 10-130172A, JP 10-179711A, JP 10-298067A, JP 10-306023A, JP 11-92361A, JP 11-104229A, JP 11-292794A and the like, and the composition for promoting lacrimal secretion of the present invention may be prepared by utilizing these techniques.

Ophthalmic Composition

The composition for promoting lacrimal secretion of the present invention can be used as an ophthalmic composition such as eyewash, eye drops, ophthalmic ointments, ophthalmic gels and the like.

In the case of an ophthalmic composition, an amount of the composition for promoting lacrimal secretion may be 0.00001-50% (w/v), preferably 0.0001-5% (w/v), and particularly 0.001-0.01% (w/v). When the amount is below 0.00001% (w/v), there is a possibility that the satisfactory lacrimal secretion promoting action is not perceived. On the other hand, when the amount exceeds 50% (w/v), there is a possibility that properties of a product itself such as the stability and the like is deteriorated. In the case of an aqueous eye drop, it is preferable that an osmotic pressure thereof is adjusted at 230-450 mOsm, and preferably 260-320 mOsm. In addition, it is suitable that a pH of an aqueous eye drop is adjusted to around 3.5-8.5, and preferably around 5.0-8.0.

It is said that an amount of lacrimal fluid on the surface of an eye is usually around 7 μL, and that a time during which an amount of a drug is decreased to a half level due to dilution or outflow by lacrimal fluid exchange on the surface of an eye is around 7 minutes. In the case of the aqueous eye drop, it is preferable that it is instilled one to several times per day, because a drug storage capacity of conjunctival sac is 10-30 μL, thereby, a large amount of the drug is not storable in the solution state.

In the case of ophthalmic topical administration, the dosage form of the composition for promoting lacrimal secretion includes solutions, ointments, ophthalmic inserting agents, gels, emulsions, suspensions and solid eye drops and the like, and may be properly selected therefrom. In addition, modifications such as sustained-releasing, stabilizing and easy-absorbing properties and the like may be further applied to such the preparations. These dosage forms are sterilized, for example, by filtration through a microorganism separating filter, heat sterilization or the like. In addition, a size of a particle contained in ophthalmic ointments or the like is preferably equal to or smaller than 75 μm.

The DDS technique may be adopted for the dosage forms as described above. For example, a DDS preparation may be prepared in which the composition for promoting lacrimal secretion of the present invention is contained in an alginic acid matrix between membranes which are controlled releasing membranes of an insoluble ethylene-vinyl acetate copolymer.

Such a DDS preparation can be continuously placed inside eyelids, and can continuously release a drug at a constant rate. A rate of releasing a drug is preferably 0.1 μg/h-10 mg/h, and more preferably 1 μg/h-100 μg/h.

In the case of an ophthalmic preparation for topical administration, a factor which influences on a contact time and a residence time of a drug becomes important. For this purpose, sustained release can be realized by adding a thickening agent to the ophthalmic preparation for topical administration, or formulating the ophthalmic preparation for topical administration into an oily or aqueous suspension, an oily solution or the like. For example, the ophthalmic preparation for topical administration can be formulated into a viscous eye drop or ophthalmic ointment with a gradually dissolving polymer (povidone and a water-soluble polymer) or the like added. In addition, sustained releasing property, absorbability and the like of a drug can be significantly enhanced by encapsulating the drug in ointments and liposomes.

The buffer to be used in the aqueous eye drop is particularly preferably a borate buffer. When the borate buffer is used as the buffer, a solution having a lower irritation as compared with the case where other buffers, for example, a phosphate buffer is used. Upon this, an amount of borate to be added is 0.01-10% (w/v), preferably 0.1-4% (w/v), and more preferably 0.5-2% (w/v).

In addition, additives such as solvents, bases, solution adjuvants, suspending agents, thickening agents, emulsifying agents, stabilizing agents, buffering agents, isotonicity adjusting agents, soothing agents, preservatives, corrigents, flavoring agents, coloring agents, excipients, binding agents, lubricants and the like can be added to a preparation, depending on the dosage forms (known dosage forms such as solutions, ointments, ophthalmic inserting agents, gels, emulsions, suspensions, solid eye drops and the like). Additionally, various additives such as pH adjusting agents, gelling agents, solubilizing agents, surfactants, sweetening agents, absorption-promoting agents, dispersing agents, preservatives, solubilizing agents and the like can be used.

Each of these additives is illustrated by way of embodiments below, but not limited thereto.

Solvents include, for example, distilled water, physiological saline solution, vegetable oils, liquid paraffin, mineral oils, propylene glycol, p-octyl dodecanol, ethanol, ethylene glycol, macrogol, glycerin, olive oil, sesame oil, peanut oil, caster oil and the like.

Isotonicity adjusting agents include, for example, sodium chloride, boric acid, sodium citrate, potassium chloride, borax, propylene glycol, glycerin, glucose, sorbitol, mannitol, trehalose and the like.

Buffering agents include, for example, boric acid, phosphoric acid, acetic acid, citric acid, carbonic acid, tartaric acid and salts thereof, borax, sodium citrate, sodium glutamate, sodium aspartate and the like.

Stabilizing agents include, for example, sodium sulfite, propylene glycol and the like.

Chelating agents includes, for example, edetic acid and salts thereof, nitrilotriacetic acid and salts thereof, trihydroxymethylaminomethane, citric acid, sodium hexametaphosphate and the like.

Thickening agents include, for example, glycerin, carboxyvinyl polymer, chondroitin sulfate, polyvinyl alcohol, polyvinyl pyrrolidone, hydroxyethyl cellulose, hydroxypropyl cellulose, methyl cellulose, hydroxypropylmethyl cellulose, carboxymethyl cellulose and salts thereof, sodium alginate, macrogol 4000, gum arabic, gelatin and the like.

Bases include, for example, vaseline, purified lanolin, zeren 50, plastibase, macrogol, liquid paraffin, polyethylene glycol, carboxymethyl cellulose and the like.

Gelling agents include, for example, carboxymethyl cellulose, methyl cellulose, carboxyvinyl polymer, ethylene maleic anhydride polymer, polyoxyethylene-polyoxypropylene block copolymer, gellan gum and the like.

Excipients include, for example, crystalline cellulose and the like.

Binding agents include, for example, hydroxypropyl cellulose, hydroxypropylmethyl cellulose, gelatin, polyvinyl pyrrolidone and the like.

Lubricants include, for example, magnesium stearate, hydrogenated caster oil, talc and the like.

Stabilizing agents include, for example, editates, sodium citrate, sodium hydrogensulfite, ethylenediaminetetraacetates and the like.

For example, pH adjusting agents include hydrochloric acid, sodium hydroxide, phosphoric acid, citric acid, malic acid, tartaric acid, fumaric acid, lactic acid, succinic acid, ascorbic acid, acetic acid and the like.

Binding agents include, for example, hydroxypropyl cellulose, hydroxypropylmethyl cellulose, gelatin and the like.

Suspending agents include, for example, methyl cellulose, sodium carboxymethyl cellulose, carboxyvinyl polymer, hydroxypropylmethyl cellulose, polyvinyl alcohol, polyvinyl pyrrolidone, polyethylene glycol, sodium chondroitin sulfate, polysorbate 80 and the like.

Bactericides include, for example, benzethonium chloride, chlorhexidine gluconate and the like.

Antioxidants include, for example, sulfites, ascorbic acid, α-tocopherol, cysteine and the like.

Coloring agents include, for example, tar pigments, riboflavin, licorice extracts, zinc oxide and the like.

Wetting agents include, for example, terpenoids (menthol, borneol, camphor, geraniol, anethole, limonene, eugenol) and the like.

In addition to the above additives, drugs such as antibiotics, antivirals, anti-inflammatory drugs, antiallergics, vasoconstrictors, local anesthetics, analgesics, intraocular pressure-lowering agents, immunoregulators, vitamins and the like can be incorporated in the composition for promoting lacrimal secretion of the present invention, so long as they does not deteriorate the object of the present invention. Such drugs are illustrated by way of embodiments below.

Antibiotics include, for example, aminoglucosides, quinolones, new quinolones, macrolides, cephems and the like.

Sulfa drugs include, for example, sulfamethoxazole, sulfisoxazole, sulfisomidine, sulfadiazine, sulfadimethoxine, sulfamethoxypyridazine and the like.

Antivirals include, for example, famciclovir, penciclovir, aciclovir and the like.

Nonsteroidal anti-inflammatory drugs include, for example, indomethacin, diclofenac, pranoprofen, tiaprofenic acid, tolfenamic acid and the like.

Steroidal anti-inflammatory drugs include, for example, prednisolone and the like.

Anti-inflammatories include, for example, dipotassium glycyrrhizinate, allantoin, ε-aminocaproic acid, berberine chloride, berberine sulfate, sodium azulenesulfonate, zinc sulfate, zinc lactate, lysozyme chloride and the like.

Antiallergics include, for example, ketotifen, oxatomide, cetirizine, sodium cromoglicate and the like.

Antihistamines include, for example, mequitazine, chlorpheniramine maleate, diphenhydramine hydrochloride and the like.

Vasoconstrictors include, for example, naphazoline, tetrahydrozoline, oxymethazoline, phenylephrine, ephedrines, epinephrine and the like, and salts thereof, and the like.

Local anesthetics include, for example, lidocaine hydrochloride, procaine hydrochloride, dibucaine hydrochloride and the like.

Cholinolytics include, for example, belladonna alkaloid, flutropium bromide, tropicamide and the like.

Antiphlogistic enzymes include, for example, lysozyme chloride, serrapeptase, bromelain and the like.

Miotics include, for example, pilocarpine hydrochloride and the like.

Galenical extracts include, for example, barren-worts, licorice, oriental bezoar, Ginseng, coix seed, Japanese angelica root, bupleurum root, cinnamon bark, schisandra fruit, lithospermum root and the like.

Flavoring agents and refreshing agents include, for example, menthols, camphors, borneols, eucaliptus, geraniols, fennels, peppermints and the like.

Anti-cholino esterases include, for example, neostigmine methylsulfate and the like.

In addition, the a composition for promoting lacrimal secretion of the present invention can be formulated into an ophthalmic composition, and in that case, the known vitamins, for example, vitamin A, vitamin C, vitamin E, vitamin $B_1$, $B_2$, $B_6$, $B_{12}$ and the like as well as derivatives thereof can be used alone or in combination of two or more thereof. Retinol as a derivative of vitamin A, ascorbates as a derivative of vitamin C, tocopherol succinate as a derivative of vitamin E, bisibutiamine as a derivative of vitamin $B_1$, flavin adenine dinucleotide as a derivative of vitamin $B_2$, salts of pyridoxine and pyridoxal as a derivative of vitamin $B_6$, hydroxocobalamin as a derivative of vitamin $B_{12}$, and the like can be used. In addition, other vitamins such as nicotinates, pantothenates, biotin and the like can be used.

In the eye drop, a preferable amount of vitamins to be added is, 0.1-10% (w/v), preferably 0.25-5% (w/v) of vitamine A and derivatives thereof, 0.01-0.5% (w/v), preferably 0.03-0.3% (w/v) of vitamin $B_1$ and derivatives thereof, 0.005-0.3% (w/v), preferably 0.01-0.2% (w/v) of vitamin $B_2$ and derivatives thereof, 0.01-0.5% (w/v), preferably 0.03-0.3% (w/v) of vitamin $B_6$ and derivatives thereof, 0.000005-0.003 (w/v), preferably 0.00001-0.0015% (w/v) of vitamin $B_{12}$ and derivatives thereof, 0.005-0.2% (w/v), preferably 0.01-0.1% (w/v) of vitamin C and derivatives thereof, and 0.005-0.2% (w/v), preferably 0.01-0.1% (w/v) of vitamin E and derivatives thereof. When nicotinic acid amide is used, the concentration thereof is preferably 0.01-1% (w/v), and more preferably 0.05-0.5% (w/v).

In addition, amino acids as an osmoregulating chemical, a nutrient source or the like, water-soluble polymers as an osmoregulating chemical, a thickening agent or the like, neutral salts as an osmoregulating chemical, lacrimal fluid ingredients equivalent or the like and the like can be added.

Amino acids include, for example, ε-aminocaproic acid, glutamic acid, lysine, histidine, leucine, methionine, phenylalanine and the like. In addition, upon incorporation of the amino acid in the aqueous eye drop composition of the present invention, the amino acids may be added as such or in the form of salts thereof. Such salts include, for example, sodium glutamate, lysine hydrochloride, histidine hydrochloride and the like. When the amino acid is used, the concentration thereof is preferably 0.01-1% (w/v), and more preferably 0.05-0.5% (w/v).

Water-soluble polymers include, for example, polyvinyl pyrrolidone, hydroxypropylmethyl cellulose, polyvinyl alcohol, carboxymethyl cellulose and the like. The concentration of the water-soluble polymer is preferably 0.1-5% (w/v), and more preferably 0.3-3% (w/v).

Neutral salts include, for example, sodium chloride, calcium chloride, magnesium chloride, sodium sulfate, calcium sulfate, magnesium sulfate, sodium nitrate, calcium nitrate and magnesium nitrate, and particularly preferred among them are sodium chloride, calcium chloride, magnesium chloride and magnesium sulfate. Preferably, the concentration of the neutral salts is determined considering the osmotic pressure.

The solution adjuvants may be used in the ophthalmic composition of the present invention. The solution adjuvants include, for example, cyclodextrin, polyvinyl pyrrolidone, caffeine, propylene glycol, benzyl benzoate, ethanol, trisaminomethane, mannitol, sodium carbonate, sodium citrate, taurine, nonionic surfactants such as polyoxyethylenesorbitan mono higher fatty acid ester (polyoxypolyoxyethylenesorbitan monooleate, polyoxyethyleneoxystearic acid triglyceride and the like), polyethylene glycol, polyoxyethylene hydrogenated castor oil, polyoxyethylenesorbitan monooleate, polyoxyethylene monostearyl, polyoxyethylene lauryl ether, monolaurate decaglycerol, polyoxyethylene polyoxypropylene glycol and the like. The nonionic surfactants to be used in the eye drop and the like are known to have a relatively low irritation for mucosa and cornea and, therefore, they are widely used. The concentration of the nonionic surfactant is preferably 0.01-10% (w/v), more preferably 0.05-5% (w/v), and yet more preferably 0.1-2% (w/v). Other surfactants include anionic surfactants (alkyl sulfate, sodium lauryl sulfate, sodium lauroyl sarcosinate), but it is not preferable that they are used in the eye drop because they have irritation for mucosa and the like, although they have the strong dissolution aiding action.

In addition, a preservative and an antiseptic are preferably contained in the ophthalmic composition. The preservative includes, for example, phenolic substances such as phenol, cresol and paraoxybenzoic acid esters, alcohols such as chlorobutanol, propylene glycol and the like, acidic substances such as benzoic acid, dehydroacetic acid and the like and salts thereof, quaternary ammonium salts such as benzalkonium chloride, benzethonium chloride and the like, polyethyleneoxide-containing high molecular quaternary ammonium compounds, thimerosal and the like.

The antiseptic is preferably prepared in the concentration between 0.0001% (w/v) and 5% (w/v), and includes, for example, quaternary ammonium salts such as benzalkonium chloride, benzethonium chloride, cetylpyridinium chloride and the like, paraoxybenzoic acid esters such as methyl paraoxybenzoate, ethyl paraoxybenzoate, propyl paraoxybenzoate, butyl paraoxybenzoate and the like, benzyl alcohol, phenethyl alcohol, chlorobutanol, thiomersal, thimerosal, methylparaben, propylparaben, disodium editate, sorbic acid and salts thereof, sodium dehydroacetate and the like.

In addition, as described above, sustained effects can be expected by using together for example an aminopeptidase inhibitor because it is known that the peptide derivatives of the present invention are degraded by peptidases in a living body. Amastatin, Arphamenine A, Arphamenine B, bestatin and the like are known as the aminopeptidase inhibitor, and these compounds may be contained in or may be used together with the preparation. Also, in the case where the component as described above is not a peptide, the substance which inactivates or degrades the component may be contained in or may be used together with the preparation to sustain the effects of the component.

For dry eye derived from abnormal lipid secretion due to meibomian glands dysfunction, a trace amount of oils such as caster oil, liquid paraffin and the like may be added in the preparation, in addition to the composition for promoting lacrimal secretion of the present invention.

Ingredients which are used in the conventional composition other than above ingredients can be used in the preparation, and an amount of these ingredients to be added may be a usual amount so long as they do not deteriorate the effects of the present invention.

When an insoluble drug or the like is contained in the composition for promoting lacrimal secretion of the present invention, known techniques such as those described in JP 11-29463A may be used to obtain a stable aqueous suspension.

Preparation for Contact Lens

The composition for promoting lacrimal secretion of the present invention can be applied to an eye drop for contact lens, a washing solution for contact lens and a preserving solution for contact lens, and a contact lens composition.

When the composition for promoting lacrimal secretion of the present invention is used as the eye drop for contact lens, the washing solution for contact lens and the preserving solution for contact lens, it is preferable that a surfactant is incorporated therein. The effect of preventing adsorption of a phospholipid-like polymer to the contact lens can be expected by incorporating the surfactant therein.

Surfactants include nonionic surfactants such as polyoxyethylene-polyoxypropylene block copolymer, polyoxyethylene/polyoxypropylene-substituted ethylenediamine, Polysorbate 80, polyoxyethylene hydrogenated castor oil, polyoxyethylenestearate and the like, amphoteric surfactants such as alkylpolyaminoethyl glycine and the like, and anionic surfactants such as alkylbenzene sulfonate, alkyl sulfate and the like and, among them, nonionic surfactants are the most preferable in light of safety to eyes. An amount of the surfactant to be incorporated is preferably 0.001-5%, and more preferably 0.01-1%.

An eye drop for contact lens, a washing solution for contact lens and a preserving solution for contact lens having a generally used composition may be used, and additives to be used therein may be properly selected from the additives described above for the ophthalmic preparation for topical administration. The eye drop for contact lens, the washing solution for contact lens and the preserving solution for contact lens may be produced according to the method similar to that as described above for the ophthalmic preparation for topical administration.

In addition, a drug-sustained releasing contact lens may be produced in which the composition for promoting lacrimal secretion of the present invention is retained in and/or adhered to a contact lens.

Contact lens may be produced using known materials. For example, materials for water-containing soft ophthalmic lens as described in JP 9-80358A, 2-hydroxyethyl methacrylate polymers as described in JP 9-124715A, ophthalmic lens materials as described in JP 9-189887A, molded ophthalmic collagen gels as described in JP 11-197234A, the hydrogel lens which is pre-coated with a lipid layer as described in JP 9-101488A and the like may be used. Additionally, known materials such as methacrylic acid ester polymers, copolymers of oligosiloxanylalkyl(meth)acrylate monomers/methacrylic acid ester monomers, and the like may be used.

Generally used contact lens such as hard or rigid cornea-type lens, and gel, hydrogel or soft-type lens which are produced from the above known materials may be used.

The drug sustained-releasing contact lens may be produced, for example, by incorporating in or adhering to the contact lens the composition for promoting lacrimal fluid secretion of the present invention according to the known methods for producing the drug sustained-releasing contact lens as described in JP 8-24325A, JP 11-24010A, JP 10-339857A and the like.

Specifically, the drug sustained-releasing contact lens may be produced by adhering to a part of the contact lens a finely-divided or gel drug sustained-releasing agent which is prepared from the active peptide and/or lacrimal secretion promoting peptide of the present invention with polymers such as polyvinyl pyrrolidone, sodium hyaluronate and the like.

In addition, the drug sustained-releasing contact lens may be produced by forming a drug reservoir such as by producing a contact lens from a member which forms a front surface of the lens and a member which forms a rear surface of the lens. Also, the contact lens of the present invention may be produced according to the known methods for producing the drug sustained-releasing contact lens other than those described above.

The present invention will be further illustrated below by way of Examples, but the present invention is not limited thereto.

EXAMPLE 1

Synthesis of Various Peptide Derivatives

1. Method for Synthesizing L-Arg-L-Leu-NH$_2$ 1.03 g (0.390 meq/g) of Fmoc-PAL-PEG-PS-resin (Applied Biosystems) was weighted, and 20 mL of dimethylformamide was added thereto to stand for 2-3 hours, and the resin was swollen and filled in a column for peptide synthesis.

The column for peptide synthesis was prepared according to the above method, and 565 mg of Fmoc-L-Leu-OH (Bachem) and 1.038 g of Fmoc-L-Arg (Pbf)-OH (Applied Biosystems) were separately weighted in a tube, and 380 mg of HATU (O-(7-azabenztriazole-1-yl)-1,1,3,3-tetramethyluronium hexafluorophosphate) (Applied Biosystems) was added to each tube. Amino acids described above were placed in an order from the C-terminal, and synthesis was performed using a peptide synthesizer PIONEER (Applied Biosystems). The synthesized peptide-resin was treated with a mixture of TFA-H$_2$O-phenol-triisopropylsilane (8.8:5.0:0.5:0.2) for 4 hours, the resin was filtrated, then the filtrate was recrystallized from cold diethyl ether (Kishida Chemical Co., Ltd.) to obtain a crude peptide. Then, the crude peptide was purified by subjecting it to HPLC (A: 0.02% TFA in water, B: 0.02% TFA in 50% CH$_3$CN). The resulting fraction containing a purified peptide was lyophilized to obtain the aimed peptide.

2. Method for Synthesizing D-Arg-L-Leu-NH$_2$ 1.03 g (0.390 meq/g) of Fmoc-PAL-PEG-PS-resin (Applied Biosystems) was weighted, and 20 mL of dimethylformamide was added thereto to stand for 2-3 hours, and the resin was swollen and filled in a column for peptide synthesis.

The column for peptide synthesis was prepared according to the above method, and 565 mg of Fmoc-L-Leu-OH (Bachem) and 1.038 g of Fmoc-D-Arg (Pbf)-OH (Bachem) were separately weighted in a tube, and 380 mg of HATU (O-(7-azabenztriazole-1-yl)-1,1,3,3-tetramethyluronium hexafluorophosphate) (Applied Biosystems) was added to each tube. Amino acids described above were placed in an order from the C-terminal, and synthesis was performed using a peptide synthesizer PIONEER (Applied Biosystems). The synthesized peptide-resin was treated with a mixture of TFA-H$_2$O-phenol-triisopropylsilane (8.8:5.0:0.5:0.2) for 4 hours, the resin was filtrated, then the filtrate was recrystallized from cold diethyl ether (Kishida Chemical Co., Ltd.) to obtain a crude peptide. Then, the crude peptide was purified by subjecting it to HPLC (A: 0.02% TFA in water, B: 0.02% TFA in 50% CH$_3$CN). The resulting fraction containing a purified peptide was lyophilized to obtain the aimed peptide.

3. Method for Synthesizing L-Arg-D-Leu-NH$_2$ 1.03 g (0.390 meq/g) of Fmoc-PAL-PEG-PS-resin (Applied Biosystems) was weighted, and 20 mL of dimethylformamide was added thereto to stand for 2-3 hours, and the resin was swollen and filled in a column for peptide synthesis.

The column for peptide synthesis was prepared according to the above method, and 565 mg of Fmoc-D-Leu-OH (Bachem) and 1.038 g of Fmoc-L-Arg (Pbf)-OH (Applied Biosystems) were separately weighted in a tube, and 380 mg of HATU (O-(7-azabenztriazole-1-yl)-1,1,3,3-tetramethyluronium hexafluorophosphate) (Applied Biosystems) was added to each tube. Amino acids described above were placed in an order from the C-terminal, and synthesis was performed using a peptide synthesizer PIONEER (Applied Biosystems). The synthesized peptide-resin was treated with a mixture of TFA-H$_2$O-phenol-triisopropylsilane (8.8:5.0:0.5:0.2) for 4 hours, the resin was filtrated, then the filtrate was recrystallized from cold diethyl ether (Kishida Chemical Co., Ltd.) to obtain a crude peptide. Then, the crude peptide was purified by subjecting it to HPLC (A: 0.02% TFA in water, B: 0.02% TFA in 50% CH$_3$CN). The resulting fraction containing a purified peptide was lyophilized to obtain the aimed peptide.

4. Method for Synthesizing D-Arg-D-Leu-NH$_2$ 1.03 g (0.390 meq/g) of Fmoc-PAL-PEG-PS-resin (Applied Biosystems) was weighted, and 20 mL of dimethylformamide was added thereto to stand for 2-3 hours, and the resin was swollen and filled in a column for peptide synthesis.

The column for peptide synthesis was prepared according to the above method, and 565 mg of Fmoc-D-Leu-OH (Bachem) and 1.038 g of Fmoc-D-Arg(Pbf)-OH (Bachem) were separately weighted in a tube, and 380 mg of HATU (O-(7-azabenztriazole-1-yl)-1,1,3,3-tetramethyluronium hexafluorophosphate) (Applied Biosystems) was added to each tube. Amino acids described above were placed in an order from the C-terminal, and synthesis was performed using a peptide synthesizer PIONEER (Applied Biosystems). The synthesized peptide-resin was treated with a mixture of TFA-H$_2$O-phenol-triisopropylsilane (8.8:5.0:0.5:0.2) for 4 hours, the resin was filtrated, then the filtrate was recrystallized from cold diethyl ether (Kishida Chemical Co., Ltd.) to obtain a crude peptide. Then, the crude peptide was purified by subjecting it to HPLC (A: 0.02% TFA in water, B: 0.02% TFA in 50% CH$_3$CN). The resulting fraction containing a purified peptide was lyophilized to obtain the aimed peptide.

5. Method for Synthesizing cyclo-L-Arg-L-Leu-NH$_2$ 1.00 g (0.2 meq/g) of L-Leu-PS-resin (Novabiochem) was weighted, and 20 mL of dimethylformamide was added thereto to stand for 2-3 hours, and the resin was filtrated. To the resin, 0.519 g of Fmoc-L-Arg (Pbf)-OH (Applied Biosystems), 600 µL of N, N-diisopropylethylamine (Aldrich) and 380 mg of HATU (O-(7-azabenztriazole-1-yl)-1,1,3,3-tetramethyluronium hexafluorophosphate) (Applied Biosystems) dissolved in 10 mL of dimethylformamide was added. After 30 minutes agitation, the resin was filtrated and washed with an appropriate amount of dimethylformamide. Furthermore, 20 mL of piperidine (WAKO) and dimethylformamide (2:8) was added to the resin and agitated for 30 minutes. Then, the resin was filtrated and washed with an appropriate amount of dimethylformamide. The synthesized peptide-resin was treated with a mixture of TFA-H$_2$O-phenol-triisopropylsilane (8.8:5.0:0.5:0.2) for 4 hours, the resin was filtrated, then the filtrate was cyclized and recrystallized with cold diethyl ether (Kishida Chemical Co., Ltd.) to obtain a crude peptide. Then, the crude peptide was purified by subjecting it to HPLC (A: 0.02% TFA in water, B: 0.02% TFA in 80% CH$_3$CN). The resulting fraction containing a purified peptide was lyophilized to obtain the aimed peptide.

6. Method for Synthesizing N-(2-furoyl)-L-Arg-L-Leu-NH$_2$ 1.03 g (0.390 meq/g) of Fmoc-PAL-PEG-PS-resin (Applied Biosystems) was weighted, and 20 mL of dimethylformamide was added thereto to stand for 2-3 hours, and the resin was swollen and filled in a column for peptide synthesis. The column for peptide synthesis was prepared according to the above method, and 565 mg of Fmoc-L-Leu-OH (Bachem) and 1.038 g of Fmoc-L-Arg(Pbf)-OH (Applied Biosystems) were separately weighted in a tube, and 380 mg of HATU (O-(7-azabenztriazole-1-yl)-1,1,3,3-tetramethyluronium hexafluorophosphate) (Applied Biosystems) was added to each tube. Amino acids described above were placed in an order from the C-terminal, and synthesis was performed using a peptide synthesizer PIONEER (Applied Biosystems). The synthesized peptide-resin was removed from the peptide synthesizer and filtrated while it was washed with dichloromethane. To the peptide-resin, 224 mg of 2-furoic acid (Aldrich), 600 µL of N,N-diisopropylethylamine (Aldrich) and 380 mg of HATU (O-(7-azabenztriazole-1-yl)-1,1,3,3- tetramethyluronium hexafluorophosphate)(Applied Biosystems) dissolved in 10 mL of dimethylformamide was added. After 30 minutes agitation, the resin was filtrated and washed with an appropriate amount of dimethylformamide. Furthermore, 20 mL of piperidine (WAKO) and dimethylformamide (2:8) was added to the resin and agitated for 30 minutes. Then, the resin is filtrated and washed with an appropriate amount of dimethylformamide. The peptide-resin thus synthesized was treated with a mixture of TFA-$H_2O$-phenol-triisopropylsilane (8.8:5.0:0.5:0.2) for 4 hours, the resin was filtrated, then the filtrate was recrystallized from cold diethyl ether (Kishida Chemical Co., Ltd.) to obtain a crude peptide. Then, the crude peptide was purified by subjecting it to HPLC (A: 0.02% TFA in water, B: 0.02% TFA in 50% $CH_3CN$). The resulting fraction containing a purified peptide was lyophilized to obtain the aimed peptide.

EXAMPLE 2

Effects of Various Peptide Derivatives on Rat Lacrimal Fluid Secretion In Vivo (1) Animals Used and Housing Environments Male Wistar rat at 6 weeks of age was used in experiments. Each animal was housed for one week under the environment of room temperature of 23±2° C., a humidity of 50±5% and a 12 hours light/dark cycle (light: 07:00-19:00) and, thereafter, it was subjected to experiments. During the housing and experiment period, the animal was fed a solid chaw and water ad lib.

(2) Method for Measuring an Amount of Lacrimal Fluid Secretion

An amount of rat lacrimal fluid secretion was measured according to the method of Iga et al. (Iga, Y. et al., Jpn. J. Pharmacol., 78, 373-80, 1998). That is, the rat was anesthetized with pentobarbital (50 mg/kg, intraabdominal administration), and a paper with 2 mm width for testing human lacrimal secretion function, the Schirmer test paper (Showa Yakuhin Kako Co., Ltd.) was inserted into a lower eyelid of the rat. After the period of time fixed has passed, the test paper was removed, and a length of a wetted portion of the test paper was measured using a caliper square to define an indicator of lacrimal secretion. An amount of lacrimal fluid was measured at 1, 2, 4 and 6 minutes after administration of the peptides.

In addition, the results are shown in the mean (mm)±standard error, and the test of significance was performed according to a Tukey's multiple comparison test.

(3) The Rat Lacrimal Secretion Promoting Action by the Peptides of the Present Invention A physiological salt solution of amastatin (2.5 µmol/kg), which is an aminopeptidase inhibitor, was intravenously administrated to the rat, and after one minute, a physiological salt solution of various peptide derivatives (5 µmol/kg) was intravenously administrated. Measurements were initiated immediately after administration of the peptides.

As a control, an amount of lacrimal secretion was also measured in the case where the physiological salt solution without the peptide (solvent) was intravenously, administrated.

The measured results of an amount of lacrimal secretion are shown in FIGS. 1-5.

Figure 2:
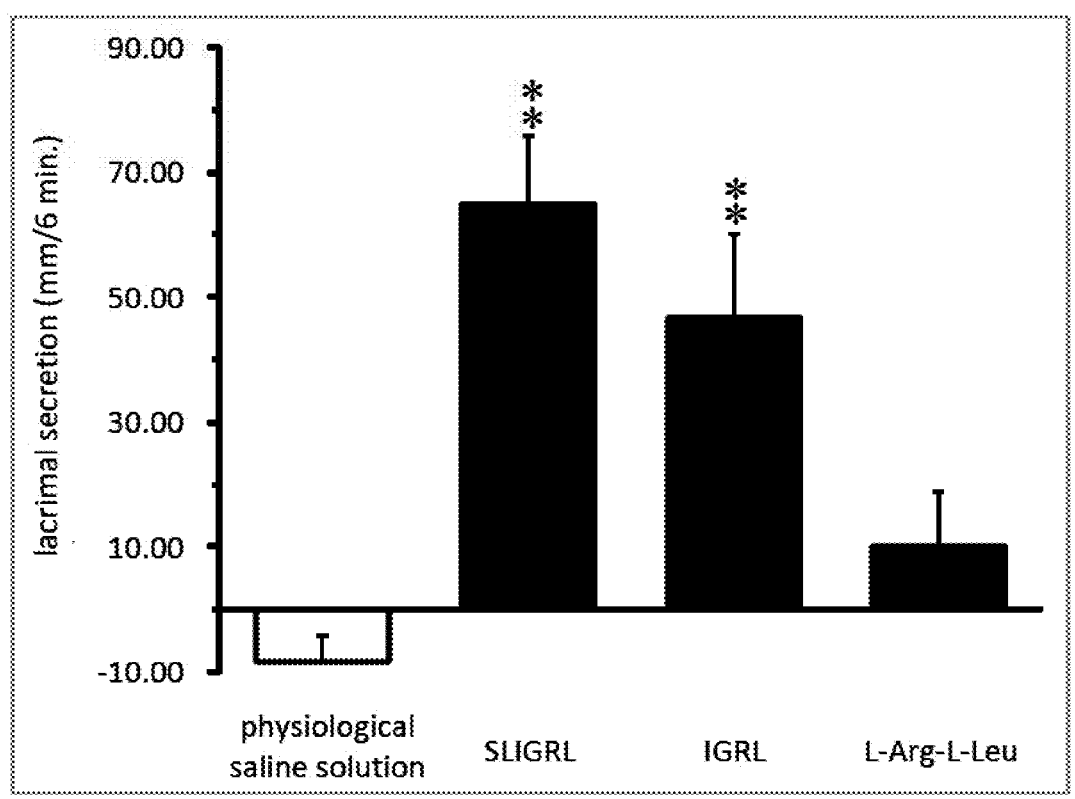
FIG. 2 is a graph showing comparison of the promoting action six minutes after administration of Ser-Leu-Ile-Gly-Arg-Leu-NH$_2$ and Ile-Gly-Arg-Leu-NH$_2$ with (L)Arg-(L)Leu-NH$_2$ on rat lacrimal secretion in vivo.
Figure 3:
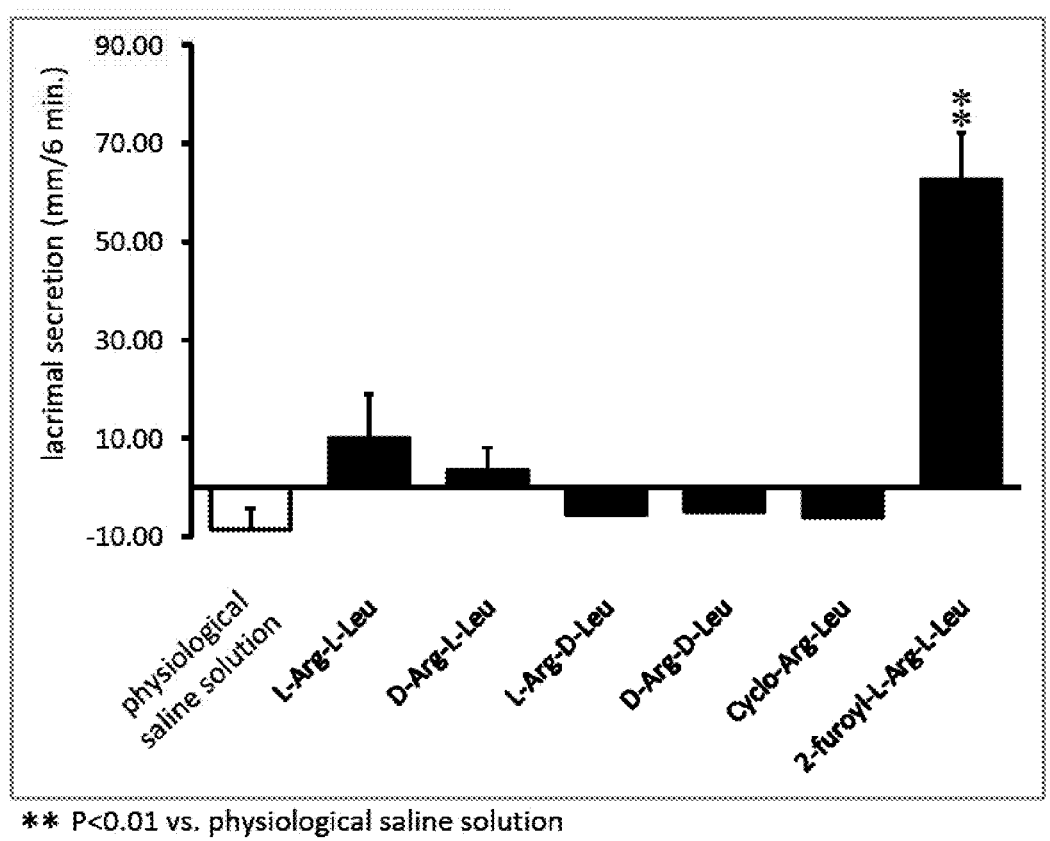
FIG. 3 is a graph showing comparison of a lacrimal secretion promoting action six minutes after administration by various amino acid derivatives in vivo.

A (L)Arg-(L)Leu-$NH_2$ was synthesized from Arg-Leu-$NH_2$ which is a part of the sequences Ser-Leu-Ile-Gly-Arg-Leu-$NH_2$ and Ile-Gly-Arg-Leu-$NH_7$ which were previously demonstrated to have the lacrimal secretion promoting action, and an affect thereof on lacrimal secretion was investigated. As the results, the (L)Arg-(L)Leu-$NH_2$ was shown to promote lacrimal secretion (FIG. 1), but its action was lower than those of Ser-Leu-Ile-Gly-Arg-Leu-$NH_2$ and Ile-Gly-Arg-Leu-$NH_2$ (FIG. 2).

It is generally known that metabolism of D-form amino acids is slower. In addition, it is known that cyclization or N-terminal modification of the peptide enhances its activity and elongates its duration of action. In the light of this, under an object of enhancement of the lacrimal secretion promoting action and elongation of duration of action, (D)Arg-(L)Leu-$NH_2$ (D- and L-form structure), (L)Arg-(D)Leu-$NH_2$ (L- and D-form structure), (D)Arg-(D)Leu-$NH_2$ (D- and D-form structure), cyclo-Arg-Leu and 2-furoyl-(L)Arg-(L)Leu-$NH_2$ (L- and L-form structure) in which a furoyl group is introduced to an N-terminal were synthesized, and the lacrimal secretion promoting action of each peptide was investigated.

Figure 4:
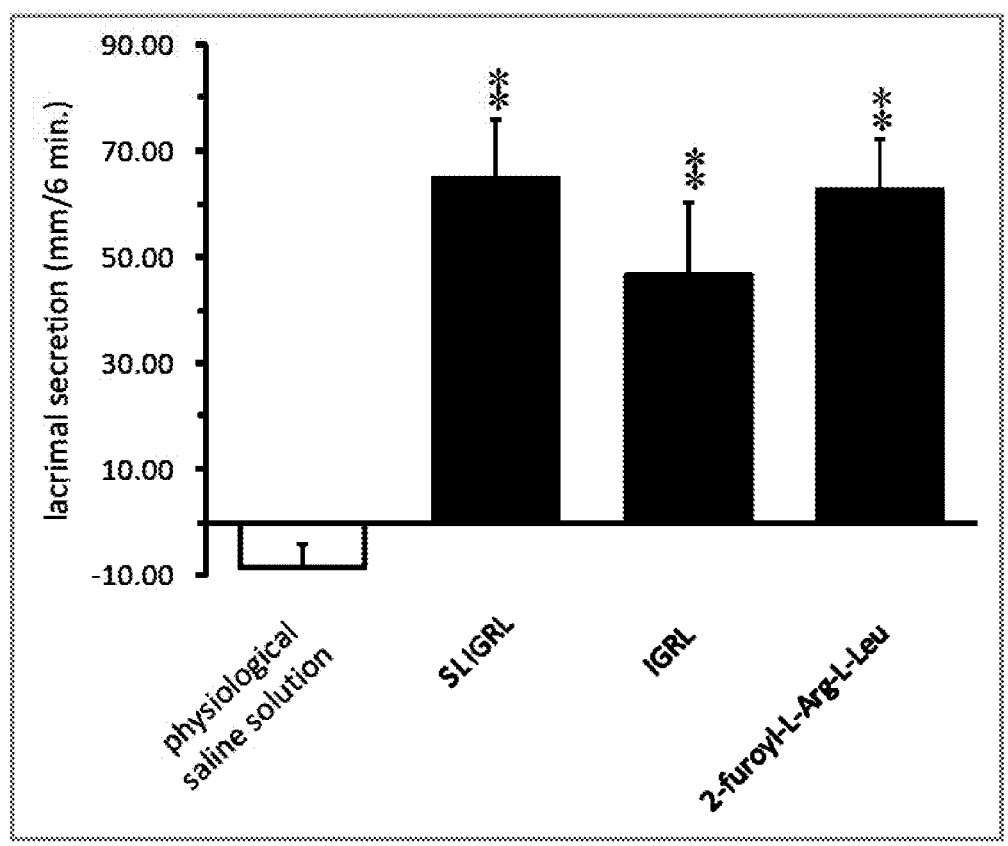
FIG. 4 is a graph showing comparison of the promoting action six minutes after administration of Ser-Leu-Ile-Gly-Arg-Leu-NH$_2$ and Ile-Gly-Arg-Leu-NH$_2$ with 2-furoyl-(L)Arg-(L)Leu-NH$_2$ on rat lacrimal secretion in vivo.
Figure 5:
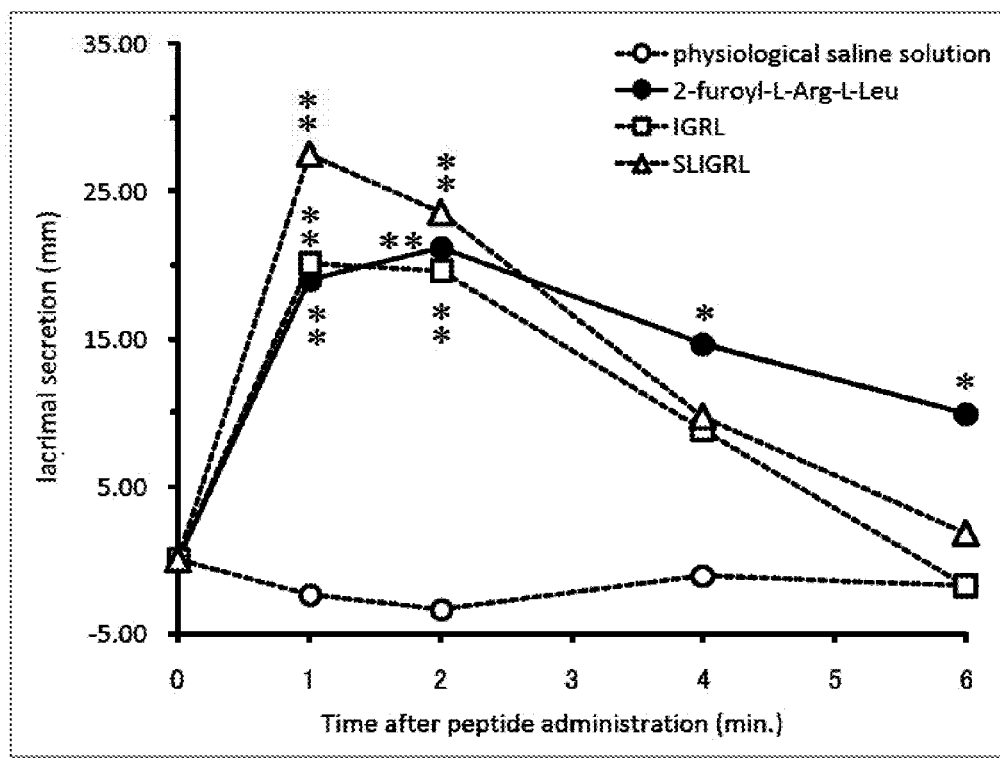
FIG. 5 is a graph showing comparison of a transient promoting action of Ser-Leu-Ile-Gly-Arg-Leu-NH$_2$ and Ile-Gly-Arg-Leu-NH$_2$ with 2-furoyl-(L)Arg-(L)Leu-NH$_2$ on rat lacrimal secretion in vivo.

As the results, (D) Arg-(L)Leu-$NH_2$, (L)Arg-(D)Leu-$NH_2$, (D)Arg-(D)Leu-$NH_2$ (D- and D-form structure) and cyclo-Arg-Leu did not entirely influence on lacrimal secretion (FIG. 3), but 2-furoyl-(L)Arg-(L)Leu-$NH_2$ showed a potent lacrimal secretion promoting action (FIG. 3), and the action thereof was almost the same as those of Ser-Leu-Ile-Gly-Arg-Leu-$NH_2$ and Ile-Gly-Arg-Leu-$NH_2$ (FIG. 4). In addition, it was shown that the lacrimal secretion promoting action exhibited by 2-furoyl-(L)Arg-(L)Leu-$NH_2$ was maintained over a longer period of time than those by Ser-Leu-Ile-Gly-Arg-Leu-$NH_2$ and Ile-Gly-Arg-Leu-$NH_2$ (FIG. 5).

It has been demonstrated that 2-furoyl-(L)Arg-(L)Leu-$NH_2$ which was synthesized from Arg-Leu which is a part of the sequences Ser-Leu-Ile-Gly-Arg-Leu-$NH_2$ and Ile-Gly-Arg-Leu-$NH_1$ has a similar degree of a lacrimal secretion promoting action to those of Ser-Leu-Ile-Gly-Arg-Leu-$NH_2$ and Ile-Gly-Arg-Leu-$NH_2$, and that duration of action thereof is longer than those of Ser-Leu-Ile-Gly-Arg-Leu-$NH_2$ and Ile-Gly-Arg-Leu-$NH_2$. In addition, absorbability into a body, which has been a problem in Ser-Leu-Ile-Gly-Arg-Leu-$NH_2$ and Ile-Gly-Arg-Leu-$NH_2$, would be enhanced in 2-furoyl-(L)Arg-(L)Leu-$NH_2$ because 2-furoyl-(L)Arg-(L)Leu-$NH_2$ has a lower molecular weight than those of Ser-Leu-Ile-Gly-Arg-Leu-$NH_2$ and Ile-Gly-Arg-Leu-$NH_2$. In addition, 2-furoyl-(L)Arg-(L)Leu-$NH_2$ has elongated duration of action as compared with that of Ser-Leu-Ile-Gly-Arg-Leu-$NH_2$ and Ile-Gly-Arg-Leu-$NH_2$ and, thereby, the problem is successfully improved.

In the light of these things, 2-furoyl-(L)Arg-(L)Leu-$NH_2$ is a therapeutic drug for abnormal lacrimal secretion diseases such as dry eye, Sjögren's syndrome and the like, having significantly excellent effects than those of Ser-Leu-Ile-Gly-Arg-Leu-$NH_2$ and Ile-Gly-Arg-Leu-$NH_2$.

INDUSTRIAL APPLICABILITY

A peptide derivative and composition for promoting lacrimal secretion of the present invention exhibits an excellent lacrimal secretion promoting action over a long period of time and, thus, is an excellent therapeutic drug for dry eye resulted from the side effect of a drug, diseases, lowered function of lacrimal secretion or the like. In addition, the peptide derivative and composition of the present invention can treat or prevent xerophthalmia, corneal afflux, foreign body feeling, itching feeling, paropsia, asthenopia, unpleasantness, burning feeling and the like followed by dry eye. In addition, the composition for promoting lacrimal secretion of the present invention can be applied to an eye drop for contact lens, a washing solution for contact lens and a preserving solution for contact lens as well as a composition of contact lens.

What is claimed is:

1. A peptide derivative represented by the formula (I):

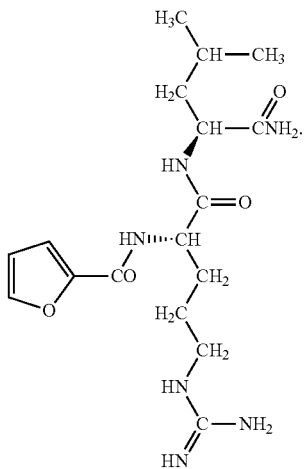

2. A composition for promoting lacrimal secretion which comprises the peptide derivative of claim 1, and is formulated such that it is pharmacologically or pharmaceutically acceptable.

3. The composition for promoting lacrimal secretion according to claim 2, which further comprises a substance that inhibits inactivation or degradation of said peptide derivative.

4. The composition for promoting lacrimal secretion according to claim 3, wherein said substance that inhibits inactivation or degradation is a peptidase inhibitor.

5. The composition for promoting lacrimal secretion according to claim 4, wherein said peptidase inhibitor is amastatin.

6. The composition for promoting lacrimal secretion according to claim 2, which is formulated into a drug delivery system (DDS) preparation.

7. The composition for promoting lacrimal secretion according to claim 2, which is formulated into a percutaneously absorbing preparation.

8. The composition for promoting lacrimal secretion according to claim 2, which is formulated into a trans-mucosally absorbing preparation.

9. The composition for promoting lacrimal secretion according to claim 2, which is an ophthalmic composition.

10. The composition for promoting lacrimal secretion according to claim 9, wherein the ophthalmic composition has a form of an eyewash, an eye drop, an ophthalmic ointment, or an ophthalmic gel.

11. The composition for promoting lacrimal secretion according to claim 9, wherein the ophthalmic composition has a form of an eye drop for contact lens, a preserving solution for contact lens or a washing solution for contact lens.

12. A contact lens which retains and/or contains the composition for promoting lacrimal secretion according to claim 2.

13. The contact lens according to claim 12, which retains and/or contains the composition for promoting lacrimal secretion such that the composition is persistently released.

14. An agent for treating an ocular disease, which comprises the composition for promoting lacrimal secretion according to claim 2, wherein the ocular disease is dry eye, ectocorneal desquamation, corneitis, corneal ulcer, or conjunctivitis.

* * * * *